US012788272B2

(12) United States Patent
Armitstead

(10) Patent No.: US 12,788,272 B2
(45) Date of Patent: Nov. 10, 2026

(54) SYSTEMS AND METHODS FOR AIDING A USER IN BREATHING USING IMPLANTABLE DEVICES

(71) Applicant: ResMed Pty Ltd, Bella Vista NSW (AU)

(72) Inventor: Jeffrey Peter Armitstead, Bella Vista NSW (AU)

(73) Assignee: ResMed Pty Ltd, Bella Vista (AU)

( * ) Notice: Subject to any disclaimer, the term of this patent is extended or adjusted under 35 U.S.C. 154(b) by 586 days.

(21) Appl. No.: 17/801,910

(22) PCT Filed: Feb. 27, 2021

(86) PCT No.: PCT/IB2021/051653
§ 371 (c)(1),
(2) Date: Aug. 24, 2022

(87) PCT Pub. No.: WO2021/171267
PCT Pub. Date: Sep. 2, 2021

(65) Prior Publication Data

US 2023/0090541 A1 Mar. 23, 2023

Related U.S. Application Data

(60) Provisional application No. 62/983,375, filed on Feb. 28, 2020.

(51) Int. Cl.
*A61B 5/08* (2006.01)
*A61B 5/00* (2006.01)
(Continued)

(52) U.S. Cl.
CPC .......... *A61B 5/0816* (2013.01); *A61B 5/0022* (2013.01); *A61B 5/6867* (2013.01);
(Continued)

(58) Field of Classification Search
CPC ..... A61B 5/0816; A61B 5/4836; A61B 5/686; A61B 5/087; A61N 1/0548; A61N 1/3601; A61N 1/3611; A61N 1/36167
See application file for complete search history.

(56) References Cited

U.S. PATENT DOCUMENTS

| | | | |
|---|---|---|---|
| 4,830,008 | A | 5/1989 | Meer |
| 2008/0027502 | A1 | 1/2008 | Ransom |

(Continued)

FOREIGN PATENT DOCUMENTS

| | | | |
|---|---|---|---|
| CA | 3072297 | A1 | 2/2019 |
| CN | 102686271 | A | 9/2012 |

(Continued)

OTHER PUBLICATIONS

International Search Report in International Patent Application No. PCT/IB2021/051653 mailed Apr. 6, 2021 (11 pp.).

(Continued)

*Primary Examiner* — Tammie K Marlen
(74) *Attorney, Agent, or Firm* — Nixon Peabody LLP

(57) ABSTRACT

A method includes receiving respiration data associated with respiration of a user from a respiration monitoring device that is positioned inside the user adjacent to a thoracic cavity of the user. The method also includes determining, based at least in part on the respiration data associated with respiration of the user, a respiration signal for the user. The method also includes determining, based at least in part on the respiration signal, a predicted start time for a future inhalation of the user. The method also includes causing a stimulation device to provide electrical stimulation to one or more branches of a nerve of the user at the predicted start time, the stimulation device being positioned inside the user adjacent to a tongue of the user and being physically separated from the respiration monitoring device.

20 Claims, 8 Drawing Sheets

(51) Int. Cl.
*A61N 1/05* (2006.01)
*A61N 1/36* (2006.01)

(52) U.S. Cl.
CPC ......... *A61N 1/0548* (2013.01); *A61N 1/3601* (2013.01); *A61N 1/3611* (2013.01); *A61N 1/36167* (2013.01)

(56) References Cited

U.S. PATENT DOCUMENTS

| | | | | |
|---|---|---|---|---|
| 2011/0112601 | A1* | 5/2011 | Meadows | A61N 1/37223 607/42 |
| 2011/0264164 | A1 | 10/2011 | Christopherson et al. | |
| 2012/0089199 | A1* | 4/2012 | Bolea | A61N 1/0558 607/42 |
| 2015/0034081 | A1 | 2/2015 | Tehrani et al. | |
| 2015/0165200 | A1* | 6/2015 | Arnold | A61N 1/37247 607/42 |
| 2017/0128002 | A1 | 5/2017 | Christopherson et al. | |
| 2017/0151432 | A1 | 6/2017 | Christopherson et al. | |
| 2018/0078761 | A1 | 3/2018 | Bolea et al. | |
| 2018/0133474 | A1 | 5/2018 | Meadows et al. | |
| 2018/0189989 | A1* | 7/2018 | Douglas | A61B 5/1124 |
| 2019/0117966 | A1* | 4/2019 | Kent | A61N 1/36139 |

FOREIGN PATENT DOCUMENTS

| | | | |
|---|---|---|---|
| JP | 2012509155 | A | 4/2012 |
| JP | 2014525280 | A | 9/2014 |
| WO | 2018/050913 | A1 | 3/2018 |

OTHER PUBLICATIONS

Written Opinion in International Patent Application No. PCT/IB2021/051653 mailed mailed Apr. 6, 2021 (6 pp.).

* cited by examiner

SYSTEMS AND METHODS FOR AIDING A USER IN BREATHING USING IMPLANTABLE DEVICES

CROSS-REFERENCE TO RELATED APPLICATIONS

This application is a U.S. National Stage of International Application No. PCT/IB2021/051653, filed Feb. 27, 2021, which claims the benefit of, and priority to, U.S. Provisional Patent Application No. 62/983,375, filed on Feb. 28, 2020, each of which is hereby incorporated by reference herein in its entirety.

TECHNICAL FIELD

The present disclosure relates generally to systems and methods for aiding a user in breathing, and more particularly, to systems and methods for aiding in preventing an apnea from occurring by stimulating one or more nerve branches at a determined stimulation time.

BACKGROUND

Many individuals suffer from sleep-related respiratory disorders such as, for example, Sleep-Disordered Breathing (SDB), Obstructive Sleep Apnea (OSA), Cheyne-Stokes Respiration (CSR). These disorders are characterized event such as apneas, hypopneas, hyperpnea, and hypercapnia where the individual's breathing stops or is disrupted/restricted during sleep. Various systems exist for aiding users experiencing sleep apnea and related respiratory disorders. Some such systems require the user to wear an interface (e.g., mask) that aids in suppling pressurized air to the airway of the user (e.g., a continuous positive airway pressure (CPAP) system). Some users find such systems to be uncomfortable, difficult to use, expensive, aesthetically unappealing, etc. Other systems rely on an implanted respiration monitoring sensor and/or stimulator that stimulates nerves/muscles to open the airway. However, these systems require a wired connection between the sensor and the simulator (e.g., wires embedded in the skin) to provide power to the sensor and/or simulator, and also to provide for communication between the sensor and stimulator. The present disclosure is directed to solving these and other problems.

SUMMARY

According to some implementations of the present disclosure, a system for aiding a user in breathing includes a respiration monitoring device, a stimulation device, a memory, and a control system. The respiration monitoring device is configured to be positioned inside the user adjacent to a thoracic cavity of the user. The respiration monitoring device includes a sensor configured to generate data associated with respiration of the user. The stimulation device is configured to be positioned inside the user adjacent to a tongue of the user. The stimulation device includes a stimulator that is configured to provide electrical stimulation to one or more branches of a nerve of the user that are adjacent to the tongue of the user. The stimulation device is physically separated from the respiration monitoring device. The memory stores machine-readable instructions. The control system includes one or more processors configured to execute the machine-readable instructions to determine, based at least in part on the generated data associated with the respiration of the user, a respiration signal for the user. The control system is further configured to identify, within the respiration signal, one or more inhalation portions and one or more exhalation portions, based at least in part on the identified one or more inhalation portions. The control system is further configured to determine a predicted start time for a future inhalation of the user. The control system is further configured to cause the stimulation device to provide electrical stimulation to the one or more branches of the nerve at a stimulation time that is based at least in part on the predicted start time for the future inhalation of the user.

According to some implementations of the present disclosure, a method includes receiving respiration data associated with respiration of a user from a respiration monitoring device, the respiration monitoring device being positioned inside the user adjacent to a thoracic cavity of the user. The method also includes determining, based at least in part on the respiration data associated with respiration of the user, a respiration signal for the user. The method also includes determining, based at least in part on the respiration signal, a predicted start time for a future inhalation of the user. The method also includes causing a stimulation device to provide electrical stimulation to one or more branches of a nerve of the user at the predicted start time, the stimulation device being positioned inside the user adjacent to a tongue of the user and being physically separated from the respiration monitoring device.

According to some implementations of the present disclosure, a system for aiding a user in breathing includes a respiration monitoring device, a stimulation device, a memory, and a control system. The respiration monitoring device is configured to be positioned inside the user adjacent to a thoracic cavity of the user and includes a sensor configured to generate data associated with respiration of the user. The stimulation device is configured to be positioned inside the user adjacent to a tongue of the user and includes a stimulator that is configured to provide electrical stimulation to one or more branches of a nerve of the user that are adjacent to the tongue of the user. The stimulation device is physically separated from the respiration monitoring device. The memory stores machine-readable instructions. The control system includes one or more processors configured to execute the machine-readable instructions to determine, based at least in part on the generated data associated with the respiration of the user, a respiration signal for the user. The control system is further configured to identify a first exhalation portion of the respiration signal. The control system is further configured to identify a start of a first inhalation portion of the respiration signal that is immediately subsequent to the first exhalation portion, the start of the first inhalation portion occurring at a start time. The control system is further configured to cause the stimulation device to provide electrical stimulation to the one or more branches of the nerve at a stimulation time that is based at least in part on the start time.

According to some implementations of the present disclosure, a method includes receiving respiration data associated with respiration of a user from a respiration monitoring device, the respiration monitoring device being positioned inside the user adjacent to a thoracic cavity of the user. The method also includes determining, based at least in part on the respiration data associated with respiration of the user, a respiration signal for the user. The method also includes identifying a start time of a first inhalation portion of the respiration signal. The method also includes causing a stimulation device to provide electrical stimulation to one or more branches of a nerve of the user at a stimulation time that is (i) subsequent to the start time and (ii) prior to a first exhalation portion of the respiration signal, the stimulation device being positioned inside the user adjacent to a tongue of the user and being physically separated from the respiration monitoring device.

According to some implementations of the present disclosure, a system for aiding a user in breathing includes a respiration monitoring device, a stimulation device, a memory, and a control system. The respiration monitoring device is configured to be positioned inside the user adjacent to a thoracic cavity of the user and includes a sensor configured to generate data associated with respiration of the user. The stimulation device is configured to be positioned inside the user adjacent to a tongue of the user and includes a stimulator that is configured to provide electrical stimulation to one or more branches of a nerve of the user that are adjacent to the tongue of the user. The stimulation device is physically separated from the respiration monitoring device. The memory stores machine-readable instructions. The control system includes one or more processors configured to execute the machine-readable instructions to determine, based at least in part on the generated data associated with the respiration of the user, a respiration signal for the user. The control system is further configured to identify a first portion of an exhalation portion of the respiration signal. The control system is further configured to identify a start of a second portion of the exhalation portion of the respiration signal, the start of the second portion of the exhalation portion occurring at a start time. The control system is further configured to cause the stimulation device to provide electrical stimulation to the one or more branches of the nerve at a stimulation time that is based at least in part on the start time The above summary is not intended to represent each implementation or every aspect of the present disclosure. Additional features and benefits of the present disclosure are apparent from the detailed description and figures set forth below.

Figure 1A:
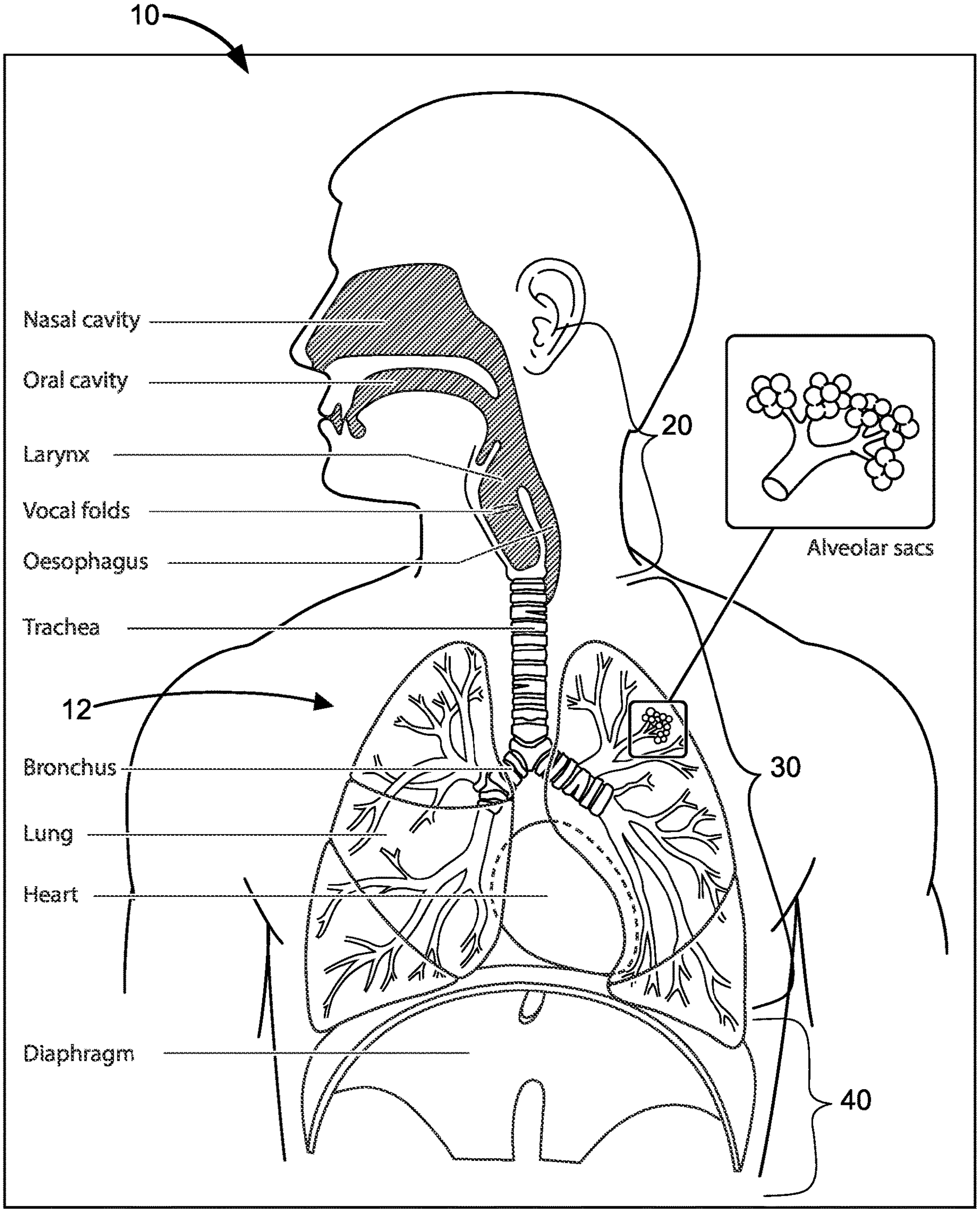
FIG. 1A is a diagram that illustrates an overview of a respiratory system of a user.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Referring to FIG. 1A, an overview of a respiratory system 12 of a user 10 (e.g., patient) is shown, which generally includes a nasal cavity, an oral cavity, a larynx, vocal folds, an esophagus, a trachea, a bronchus, lungs, alveolar sacs, a heart, and a diaphragm. More generally, the user 10 has a throat 20, which includes a region(s) of the respiratory system 12 of the user 10 generally in the neck area of the user 10. The diaphragm of the user 10 is a sheet of muscle that extends across the bottom of the rib cage of the user 10. The diaphragm generally separates the thoracic cavity 30 of the user 10, which contains the heart, lungs, and ribs, from the abdominal cavity 40 of the user 10. As the diaphragm contracts, the volume of the thoracic cavity 30 increases and air is drawn into the lungs.

As is described herein, one or more stimulators of the present disclosure can be placed (e.g., implanted via surgery, injected via syringe, etc.) inside the user 10 to aid the user 10, for example, in breathing while sleeping. For example, one or more stimulators can be positioned inside the user 10 adjacent to a tongue 16 of the user 10. In another example, one or more stimulators can be positioned inside the user 10 adjacent to a nerve (e.g., hypoglossal nerve 18) and/or nerve branches. The hypoglossal nerve 18 is generally involved in controlling movement of the tongue 16 and includes a plurality of nerve branches distributed to the extrinsic and intrinsic muscles of the tongue 16.

Figure 1B:
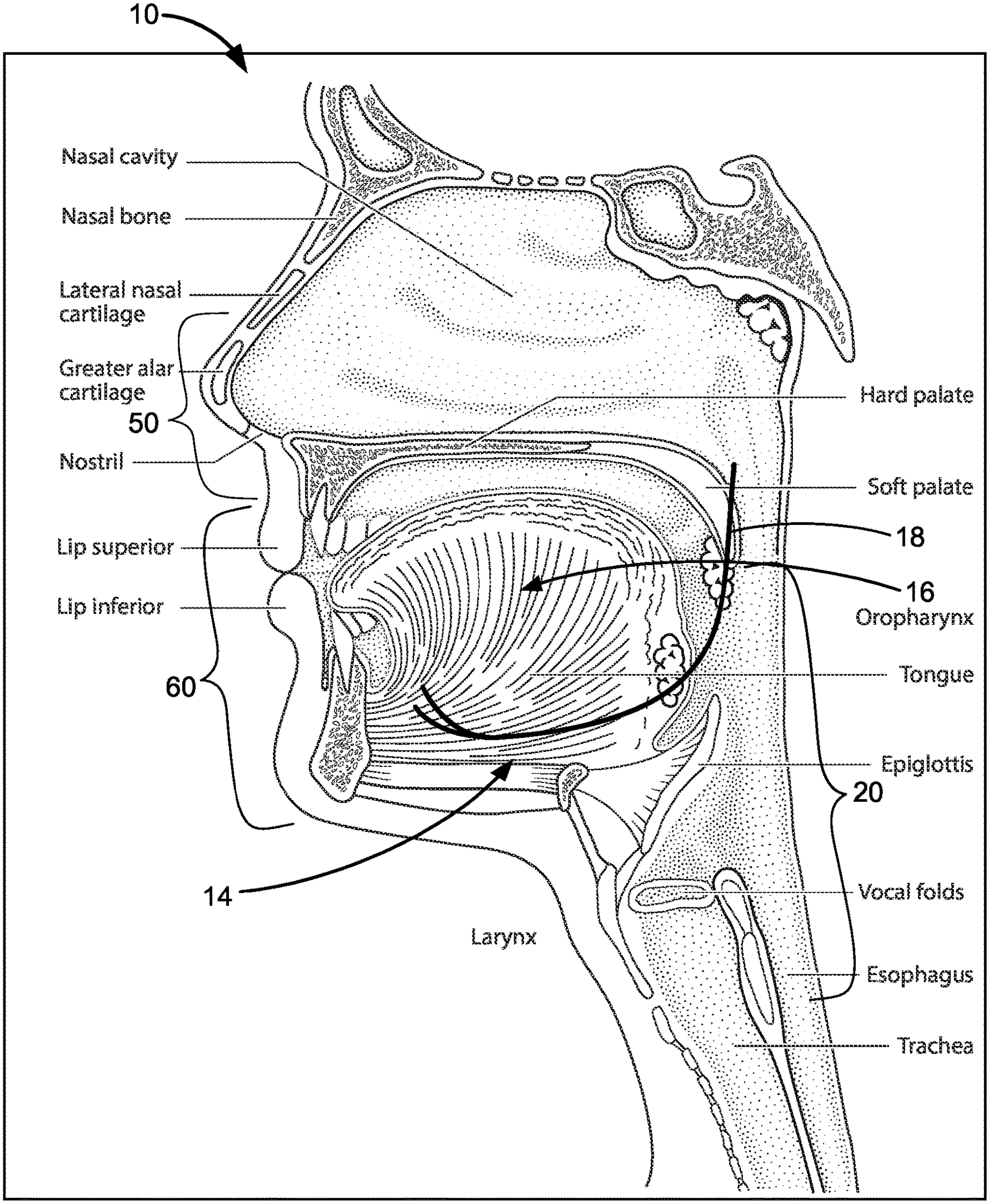
FIG. 1B is a diagram that illustrates an upper airway of the user of FIG. 1A.

Referring to FIG. 1B, a view of an upper airway 14 of the user 10 is shown, which includes the nasal cavity, nasal bone, lateral nasal cartilage, greater alar cartilage, nostrils (one shown), a lip superior, a lip inferior, the larynx, a hard palate, a soft palate, an oropharynx, a tongue, an epiglottis, the vocal folds, the esophagus, and the trachea.

The respiratory system 12 of the user 10 facilitates gas exchange. The nose 50 and mouth 60 of the user 10 form the entrance to the airways of the user 10. As best shown in FIG. 1A, the airways include a series of branching tubes, which become narrower, shorter, and more numerous as they penetrate deeper into the lungs of the user 10. The prime function of the lungs is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lungs is where the gas exchange takes place, and is referred to as the respiratory zone.

A range of respiratory disorders exist that can impact the user 10. Certain disorders are characterized by particular events (e.g., apneas, hypopneas, hyperpneas, or any combination thereof). Examples of sleep-related and/or respiratory disorders include Periodic Limb Movement Disorder (PLMD), Restless Leg Syndrome (RLS), Sleep-Disordered Breathing (SDB), Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), and chest wall disorders.

Obstructive Sleep Apnea (OSA) is a form of Sleep Disordered Breathing (SDB), and is characterized by events including occlusion or obstruction of the upper air passage during sleep resulting from a combination of an abnormally small upper airway and the normal loss of muscle tone in the region of the tongue, soft palate and posterior oropharyngeal wall. More generally, an apnea generally refers to the cessation of breathing caused by blockage of the air (Obstructive Sleep Apnea) or the stopping of the breathing function (often referred to as central apnea). Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration.

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterized by repetitive de-oxygenation and re-oxygenation of the arterial blood. It is possible that CSR is harmful because of the repetitive hypoxia. In some users, CSR is associated with repetitive arousal from sleep, which causes severe sleep disruption, increased sympathetic activity, and increased afterload.

Respiratory failure is an umbrella term for respiratory disorders in which the lungs are unable to inspire sufficient oxygen or exhale sufficient $CO_2$ to meet the user's needs. Respiratory failure may encompass some or all of the following disorders. A user with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) encompasses many diseases and ailments that impair the functioning of the muscles either directly via intrinsic muscle pathology, or indirectly via nerve pathology. Some users suffering from NMD are characterized by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) rapidly progressive disorders: characterized by muscle impairment that worsens over months and results in death within a few years (e.g. amyotrophic lateral sclerosis (ALS) and duchenne muscular dystrophy (DMD) in teenagers); (ii) variable or slowly progressive disorders: characterized by muscle impairment that worsens over years and only mildly reduces life expectancy (e.g. limb girdle, Facioscapulohumeral and myotonic muscular dystrophy). Symptoms of respiratory failure in NMD include: increasing generalized weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterized by a restrictive defect and share the potential of long term hypercapnic respiratory failure. Scoliosis and/or kyphoscoliosis may cause severe respiratory failure. Symptoms of respiratory failure include: dyspnea on exertion, peripheral edema, orthopnea, repeated chest infections, morning headaches, fatigue, poor sleep quality and loss of appetite.

These other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping. While these other sleep-related disorders may have similar symptoms as insomnia, distinguishing these other sleep-related disorders from insomnia is useful for tailoring an effective treatment plan distinguishing characteristics that may call for different treatments. For example, fatigue is generally a feature of insomnia, whereas excessive daytime sleepiness is a characteristic feature of other disorders (e.g., PLMD) and reflects a physiological propensity to fall asleep unintentionally.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

One of more of the disorders described herein can be treated using electrical stimulation. For example, a stimulator can provide electrical and/or magnetic stimulation to the user (e.g., a nerve, nerve branch, a muscle, etc.) to aid in preventing an apnea event about to be experienced by the user. The electrical stimulation is able to aid in preventing apneas by, for example, causing the one or more muscles to move (e.g., contract) and open the airway of the user prior to an apnea occurring. For example, the stimulator can electrically stimulate the hypoglossal nerve 18 (FIG. 1B) to move the tongue 16 to aid in opening the airway to allow more inspiration and prevent apneas from occurring.

In typical stimulation systems, the stimulator is placed (e.g., implanted) in the user. A respiratory sensor is also placed in or on the user and measures the respiration of the user. The timing of the stimulation is determined based on the respiration data. In other words, the system needs to determine when to stimulate in substantially real-time based on the respiration data. Thus, in these systems, the stimulator and the respiratory sensor are electrically coupled via one or more leads and/or wires for communication (e.g., so the respiratory sensor can signal the simulator when to stimulate) and for power (e.g., to provide power to the respiratory sensor and/or the stimulator). These leads/wires are often embedded or tunneled in the skin of the user and are therefore often painful or bothersome to the user. The leads/wires are also susceptible to breaking (e.g., the wires can get stuck in the tissue or pull apart if there is not enough slack), potentially necessitating another procedure/surgery to repair the connection. The wired connection also imposes a practical limitation on the number of sensors and/or simulators (e.g., for redundancy) that can be used because this would require additional wires/leads embedded in the user's skin.

Figure 2:
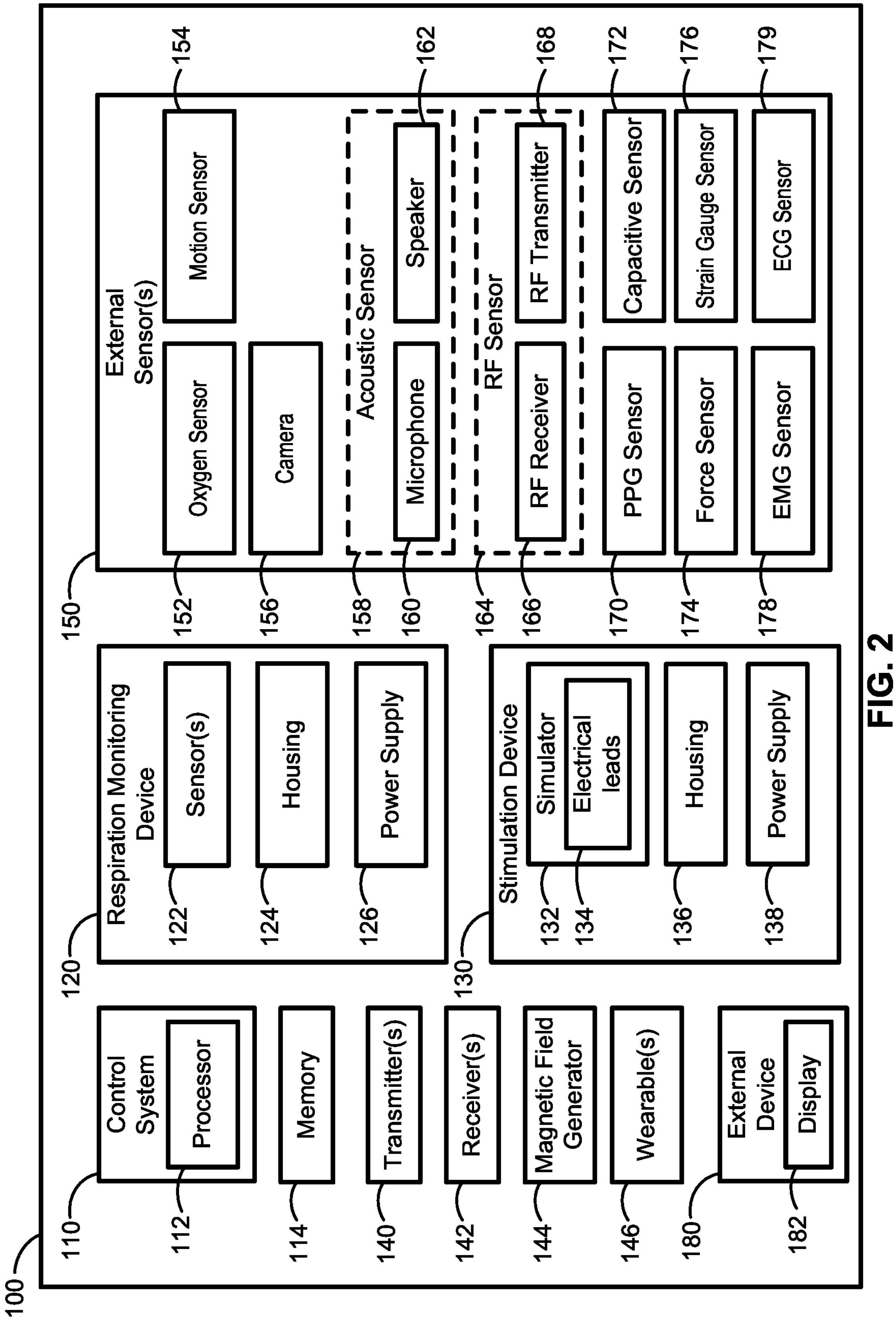
FIG. 2 is a block diagram of a system for aiding a user (e.g., in breathing), according to some implementations of the present disclosure.

Referring to FIG. 2, a system 100, according to some implementations of the present disclosure, is illustrated. The system 100 includes a control system 110, a memory device 114, a respiration monitoring device 120, a stimulation device 130, one or more transmitters 140 (hereinafter, transmitter 140), one or more receivers 142 (hereinafter, receiver 142), a magnetic field generator 144, a wearable 146, one or more external sensors 150, and an external device 180.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 can be coupled to and/or positioned within, for example, a housing of the external device 180, within a housing 124 of the respiration monitoring device 120, a housing 136 of the stimulation device 130, or any combination thereof. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within the housing of the respiration monitoring device 120, within the housing 136 of the stimulation device 130, or any combination thereof. Like the control system 110, the memory device 114 can be centralized (within one such housing) or decentralized (within two or more of such housings, which are physically distinct).

In some implementations, the memory device 114 (FIG. 1) stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family history of insomnia or sleep apnea, an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

While the control system 110 and the memory device 114 are described and shown in FIG. 2 as being a separate and distinct component of the system 100, in some implementations, the control system 110 and/or the memory device 114 are integrated in the external device 180, the respiration monitoring device 120 and/or the stimulation device 130. Alternatively, in some implementations, the control system 110 or a portion thereof (e.g., the processor 112) can be located in a cloud (e.g., integrated in a server, integrated in an Internet of Things (IOT) device, connected to the cloud, be subject to edge cloud processing, etc.), located in one or more servers (e.g., remote servers, local servers, etc., or any combination thereof.

Some of the elements of the system 100 are positioned in the user 10 (e.g., implanted in the user 10) and others of the elements of the system 100 are positioned outside the user 10 (e.g., worn/donned by the user 10). One or more of the elements of the system 100 that are positioned in the user 10 can be so positioned by being injected into the user 10 using, for example, a syringe with a hypodermic needle attached thereto. Alternatively or additionally, one or more of the elements of the system 100 that are positioned in the user 10 can be so positioned by being surgically placed therein (e.g., cutting open the skin and positioning the element(s) therein and suturing the skin closed).

The respiration monitoring device 120 includes one or more sensors 122, a housing 124, and a power supply 126. As described herein, the respiration monitoring device 120 can be placed (e.g., surgically) inside the user (e.g., in or adjacent to a thoracic cavity of the user), and the one or more sensors 122 generate data associated with respiration of the user for determining a respiration signal for the user.

The one or more sensors 122 can include any suitable sensor(s) for generated data from which a respiration signal of the user can be determined (e.g., a signal indicative of inhalation and/or exhalation of the user). In some implementations, the one or more sensors 122 includes an air pressure sensor (e.g., barometric pressure sensor, gauge, absolute transducer, etc.) that generates data indicative of the respiration (e.g., inhaling and/or exhaling) of the user. The pressure sensor can be, for example, a capacitive sensor, an electromagnetic sensor, a piezoelectric sensor, a strain-gauge sensor, an optical sensor, a potentiometric sensor, or any combination thereof. In some implementations, the one or more sensors 122 includes an air flow sensor that generates data indicative the respiration (e.g., inhaling and/or exhaling) of the user. In some implementations, the one or more sensors 122 includes a motion sensor that generates motion data indicative the respiration (e.g., inhaling and/or exhaling) of the user. In some implementations, the one or more sensors 122 includes an acoustic sensor (e.g., including a microphone and/or a speaker) that generates data indicative of the respiration (e.g., inhaling and/or exhaling) of the user. In other implementations, the one or more sensors 122 includes an electromyography (EMG) sensor that generates data indicative of the respiration (e.g., inhaling and/or exhaling) of the user. In some implementations, the one or more sensors 122 includes a photoplethysomgram (PPG) sensor that generates data indicative of the respiration (e.g., inhaling and/or exhaling) of the user. In other implementations, the one or more sensors 122 includes an oxygen sensor that generates data indicative of a blood oxygen level or oxygen saturation ($SpO_2$), which in turn are indicative of respiration (e.g., inhaling and/or exhaling) of the user.

In some implementations, the one or more sensors 122 of the respiration monitoring device 120 are directly positioned in the user 10. In such implementations, the housing 124 is not required. Alternatively, the sensor(s) 122 or a portion thereof are coupled to the housing 124 (e.g., positioned at least partially therein) and the housing 124 (with the sensor(s) 122 coupled thereto) is positioned in the user 10. The housing 124 can have the shape of an elongated pill (or any other shape) that is conducive to being injected into the user 10 using, for example, a syringe with a hypodermic needle attached thereto. In some implementations, the housing 124 electrically insulates at least a portion of the sensor(s) 122 from surrounding tissue of the user 10.

The sensor(s) 122 can be powered by the power supply 126. The power supply 126 can be, for example, a battery (e.g., a rechargeable battery). In some implementations, the power supply 126 can be recharged by the magnetic field generator 144 and/or the external device 180. Alternatively to the respiration monitoring device 120 including the power supply 126, in some implementations, power for the sensor(s) is supplied wirelessly by the magnetic field generator 144 (which can be included in the external device 180) directly to the electrical sensor(s).

In addition to the sensor(s) 122 and power supply 126 being coupled to or integrated in the housing 124, a number of other elements of the system 100 can be coupled to the housing 124 and placed into the user 10. By coupled to the housing 124 it is meant that the element coupled to the housing 124 is completely incased within the housing 124, attached to an exterior surface of the housing 124, partially protruding from one or more openings in the housing 124, directly or indirectly attached to the housing 124, or any combination thereof. For example, in some implementations, one or more of the transmitters 140 and/or one or more of the receivers 142 can be coupled to or integrated in the housing 124.

In such implementations, the transmitter 140 and/or receiver 142 allow the respiration monitoring device 120 to wirelessly communicate (e.g., using a Bluetooth communication protocol, a WiFi communication protocol, or any other suitable RF communication protocol) with the control system 110, the stimulation device 130, the external device 180 or any combination thereof (e.g., to transmit data generated by the sensor(s) 122 for analysis by the control system 110). If Bluetooth is used the wireless communication frequency is in the MHz range, whereas breaching frequency is about 15 Hz. Thus, the data the respiration monitoring device 120 can be wirelessly transmitted (e.g., to the control system 110) before the next inhalation and/or exhalation of the user.

The stimulation device 130 includes a simulator 132, a housing 136, and a power supply 138. As described herein, the stimulation device 130 can be placed (e.g., surgically) inside the user (e.g., adjacent to a tongue of the user) to stimulate one or more branches of a nerve (e.g., a hypoglossal nerve) at a determined stimulation time.

The stimulator 132 is positioned in the user 10 such that one or more electrical leads 134 of the stimulator 132 are positioned adjacent to one or more muscles of the user 10 and/or one or more nerves of the user 10 that are connected to the one or more muscles of the user 10. In some implementations, the one or more electrical leads 134 includes a first electrical lead that is positioned to stimulate a first one of the one or more muscles and/or a first one of the one or more nerves. Similarly, a second electrical lead is positioned to stimulate a second one of the one or more muscles and/or a second one of the one or more nerves. In some implementations, the first electrical lead provides the electrical stimulation at a first frequency and the second electrical lead provides the electrical stimulation at a second frequency that is different from the first frequency. In some implementations, the first electrical lead provides the electrical stimulation at a first intensity and the second electrical lead provides the electrical stimulation at a second intensity that is different from the first intensity. Alternatively, the stimulator 132 may be leadless, with the stimulator body being conductive and the ends of the body acting as electrodes.

Once the stimulation device 130 is positioned in the user 10, the stimulator 132 is capable of delivering electrical and/or magnetic stimulation to the user 10 to aid in causing the one or more muscles of the user 10 to contract. The contraction of the one or more muscles of the user 10 can aid in opening an airway of the user 10. The contraction can alternatively or additionally aid in causing the user 10 to have breathing effort (e.g., causing the diaphragm to draw/suck in air). The electrical stimulation can be applied directly to the one or more muscles of the user 10 (e.g., muscles in the tongue of the user 10, muscles surrounding and/or adjacent to the tongue of the user 10, neck muscles, throat muscles, the palate, other soft issue generally in or around the airway of the user, etc.) and/or directly to the one or more nerves that are connected to the one or more muscles. Directing the electrical stimulation to the one or more nerves (as opposed to the one or more muscles directly) allows for a relatively lower intensity (e.g., voltage, amperage, etc. or any combination thereof) of the electrical stimulation to be applied to cause the one or more muscles (connected to the one or more nerves) to contract.

The stimulator 132 includes or is an electrical conductor (e.g., one or more electrically conductive wires with or without a portion being electrically insulated). The stimulator 132 includes the one or more electrical leads 134, which are capable of carrying and/or flowing and delivering electrical current to the one or more muscles and/or one or more nerves of the user 10. The electrical current can be supplied by the power supply 138. The power supply 138 can be, for example, a battery (e.g., a rechargeable battery). In some implementations, the power supply 138 can be recharged or energized by the magnetic field generator 144 and/or the external device 180. Alternatively to the stimulator 132 including the power supply 138, in some implementations, the electrical current is supplied wirelessly by the magnetic field generator 144 (which can be included in the external device 180) directly to the electrical conductor(s).

In some implementations, the stimulator 132 only includes one or more electrically conductive wires, with or without a portion being electrically insulated. In some such implementations, the stimulator 132 has a length between about 1 millimeter and about 100 centimeters; between about 1 millimeter and about 100 millimeters; between about 1 millimeter and about 10 millimeters; or any length therebetween. Further, in some such implementations, the stimulator 132/wire has a diameter between about 0.01 millimeters and about 5 millimeters; between about 0.1 millimeter and about 2 millimeters; between about 0.1 millimeter and about 1 millimeter; or any diameter therebetween. The size and shape of the stimulator 132 can be selected to permit the injection of the stimulation device 130 into the user 10 via a syringe with an attached hypodermic needle.

In some implementations, the stimulator 132 is directly positioned in the user 10. In such implementations, the housing 136 is not required. Alternatively, the stimulator 132 or a portion thereof is coupled to the housing 136 (e.g., positioned at least partially therein) and the housing 136 (with the stimulator 132 coupled thereto) is positioned in the user 10. The housing 136 can have the shape of an elongated pill (or any other shape) that is conducive to being injected into the user 10 using, for example, a syringe with a hypodermic needle attached thereto. In some implementations, the housing 136 electrically insulates at least a portion of the stimulator 132 (e.g., the entire stimulator 132 except for the one or more electrical leads 134 or conductive ends) from surrounding tissue of the user 10.

In addition to the stimulator 132 being coupled to the housing 136, a number of other elements of the system 100 can be coupled to the housing 136 and placed into the user 10. By coupled to the housing 136 it is meant that the element coupled to the housing 136 is completely incased within the housing 136, attached to an exterior surface of the housing 136, partially protruding from one or more openings in the housing 136, directly or indirectly attached to the housing 136, or any combination thereof. For example, in some implementations, one or more of the transmitters 140 and/or one or more of the receivers 142 can be coupled to or integrated in the housing 136. In such implementations, the transmitter 140 and/or receiver 142 allow the respiration monitoring device 120 to wirelessly communicate (e.g., using a Bluetooth communication protocol, a WiFi communication protocol, or any other suitable RF communication protocol) with the control system 110, the respiration monitoring device 120, or any combination thereof (e.g., to transmit a signal to actuate the stimulator 132 to deliver electrical stimulation). In other implementations, the transmitter 140 and the receiver 142 are combined as a transceiver.

In some implementations, the stimulation device 130 can be configured to automatically stimulate the user even if the respiration monitoring device 120 has failed (e.g., the respiration monitoring device 120 has ran out of battery or is no longer receiving power from the magnetic field generator 144). In such implementations, the stimulation device 130 can be configured to stimulate at a 50% duty cycle to continue to stimulate the tongue and to aid in keeping the airway clear during inspiration. While the stimulation may not occur at the optimal stimulation time and this may consume more power in the stimulation device 130, the user will receive at least some benefit from the automatic stimulation. The user can be alerted to any failures (e.g., of the respiration monitoring device 120) by the external device 180.

While the system 100 has been described herein as including one respiration monitoring device 120, the system 100 more generally can include any suitable number of respiration monitoring devices that are the same as, or similar to, the respiration monitoring device 120 (e.g., 2, 3, 5, 10, etc.). Having multiple respiration monitoring devices can be advantageous, for example, to provide redundancy in case another respiration monitoring device fails (e.g., runs out of battery or power) and to provide more respiration data for more accurate determinations of the respiration signal. The respiration monitoring devices can be positioned in the user together in the same implant or implanted separately in the same area.

The wearable(s) 146 can be worn by the user and are generally used to position the magnetic field generator 144 adjacent to the respiration monitoring device 120 and/or the stimulation device 130 to provide power as described herein. The wearable(s) 146 can include a belt, a collar, a patch (e.g., an adhesive patch), clothing, a sleeve, a bracelet, a necklace, a watch, or any combination thereof. The magnetic field generator 144 can be embedded in the wearable 146 and/or removable from the wearable 146.

The one or more external sensors 150 of the system 100 can be used to validate data from the respiration monitoring device 120 and/or to generate or obtain different physiological data associated with the user. In some implementations, the one or more external sensors 150 can be used instead of the respiration monitoring device 120 to generate data associated with respiration of the user. The one or more external sensors 150 can include an oxygen sensor 152, a motion sensor 154, a camera 156, an acoustic sensor 158, a radio-frequency (RF) sensor 164, a PPG sensor 170, a capacitive sensor 172, a force sensor 174, a strain gauge sensor 176, an EMG sensor 178, and an electrocardiogram (ECG) sensor 179, or any combination thereof. Data from the sensor(s) 150 can be received and stored in the memory device 114 or one or more other memory devices.

The oxygen sensor 152 outputs oxygen data indicative of an oxygen concentration of gas (e.g., in the blood of the user). The oxygen sensor 152 can be, for example, a pulse oximeter sensor an ultrasonic oxygen sensor, an electrical oxygen sensor, a chemical oxygen sensor, an optical oxygen sensor, or any combination thereof.

The motion sensor 154 outputs motion data that is indicative of movement of the user. The motion data from the motion sensor 154 can be used by the control system 110 to determine movement of the user (e.g., respiration). The camera 156 outputs image data reproducible as one or more images (e.g., still images, video images, thermal images, or a combination thereof) that can be stored in the memory device 114. The image data from the camera 156 can be used by the control system 110 to determine movement of the user (e.g., respiration).

The microphone 160 outputs sound data that can be stored in the memory device 114 and/or analyzed by the processor 112 of the control system 110. The microphone 160 can be used to record sound(s) to determine (e.g., using the control system 110) a respiration signal for the user. The speaker 162 outputs sound waves that are audible to a user of the system 100. The speaker 162 can be used, for example, as an alarm clock or to play an alert or message to the user.

In some implementations, the microphone 160 and the speaker 162 can be combined into an acoustic sensor 158, as described in, for example, WO 2018/050913, which is hereby incorporated by reference herein in its entirety. In such implementations, the speaker 162 generates or emits sound waves at a predetermined interval and the microphone 160 detects the reflections of the emitted sound waves from the speaker 162. The sound waves generated or emitted by the speaker 162 have a frequency that is not audible to the human ear (e.g., below 20 Hz or above around 18 kHz). Based at least in part on the data from the microphone 160 and/or the speaker 162, the control system 110 can determine movement of the user (e.g., respiration).

The RF transmitter 168 generates and/or emits radio waves having a predetermined frequency and/or a predetermined amplitude (e.g., within a high frequency band, within a low frequency band, long wave signals, short wave signals, etc.). The RF receiver 166 detects the reflections of the radio waves emitted from the RF transmitter 168, and this data can be analyzed by the control system 110 to determine movement of the user. While the RF receiver 166 and RF transmitter 168 are shown as being separate and distinct elements in FIG. 2, in some implementations, the RF receiver 166 and RF transmitter 168 are combined as a part of an RF sensor 164. In some such implementations, the RF sensor 164 includes a control circuit. The specific format of the RF communication could be WiFi, Bluetooth, etc.

In some implementations, the RF sensor 164 is a part of a mesh system. One example of a mesh system is a WiFi mesh system, which can include mesh nodes, mesh router(s), and mesh gateway(s), each of which can be mobile/movable or fixed. In such implementations, the WiFi mesh system includes a WiFi router and/or a WiFi controller and one or more satellites (e.g., access points), each of which include an RF sensor that the is the same as, or similar to, the RF sensor 164. The WiFi router and satellites continuously communicate with one another using WiFi signals. The WiFi mesh system can be used to generate motion data based on changes in the WiFi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The PPG sensor 170 outputs physiological data associated with the user that can be used to determine, for example, a heart rate, a heart rate variability, a cardiac cycle, respiration rate, an inspiration amplitude, an expiration amplitude, an inspiration-expiration ratio, estimated blood pressure parameter(s), or any combination thereof.

The capacitive sensor 172, the force sensor 174, and the strain gauge sensor 176 output data that can be stored in the memory device 114 and used by the control system 110 to determine movement of the user (e.g., respiration). The EMG sensor 178 outputs physiological data associated with electrical activity produced by one or more muscles. The ECG sensor 179 outputs physiological data associated with electrical activity of the heart of the user. In some implementations, the ECG sensor 179 includes one or more electrodes that are positioned on or around a portion of the user.

While shown separately in FIG. 1, any combination of the one or more sensors 130 can be integrated in and/or coupled to any one or more of the components of the system 100, including the respiration monitoring device 120, the stimulation device 130, the control system 110, the external device 180, or any combination thereof.

In some implementations, the one or more external sensors 150 also include one or more of a temperature sensor, an EEG sensor, an analyte sensor, a moisture sensor, and a Light Detection and Ranging (LiDAR) sensor. The LiDAR sensor can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor can measure and map an area extending 5 meters or more away from the sensor. The LiDAR data can be fused with point cloud data estimated by an electromagnetic RADAR sensor, for example. The LiDAR sensor(s) can also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

The external device 180 (FIG. 2) includes a display device 182. The external device 180 can be, for example, a mobile device such as a smart phone, a tablet, a laptop, or the like. Alternatively, the external device 180 can be an external sensing system, a television (e.g., a smart television) or another smart home device (e.g., a smart speaker(s) such as Google Home, Amazon Echo, Alexa etc.). In some implementations, the external device 180 is a wearable device (e.g., a smart watch). The display device 182 is generally used to display image(s) including still images, video images, or both. In some implementations, the display device 182 acts as a human-machine interface (HMI) that includes a graphical user interface (GUI) configured to display the image(s) and an input interface. The display device 182 can be an LED display, an OLED display, an LCD display, or the like. The input interface can be, for example, a touchscreen or touch-sensitive substrate, a mouse, a keyboard, or any sensor system configured to sense inputs made by a human user interacting with the external device 180. In some implementations, one or more external devices can be used by and/or included in the system 100.

While system 100 is shown as including all of the components described above, more or fewer components can be included in a system for aiding a user (e.g., in breathing) according to implementations of the present disclosure. For example, a first alternative system includes the control system 110, the memory device 114, the respiration monitoring device, and the stimulation device. As another example, a second alternative system includes the control system 110, the memory device 114, the respiration monitoring device 120, the stimulation device 130, and the external device 180. As yet another example, a third alternative system includes the respiration monitoring device 120 and the stimulation device 130. Thus, various systems can be formed using any portion or portions of the components shown and described herein and/or in combination with one or more other components.

Figure 3A:
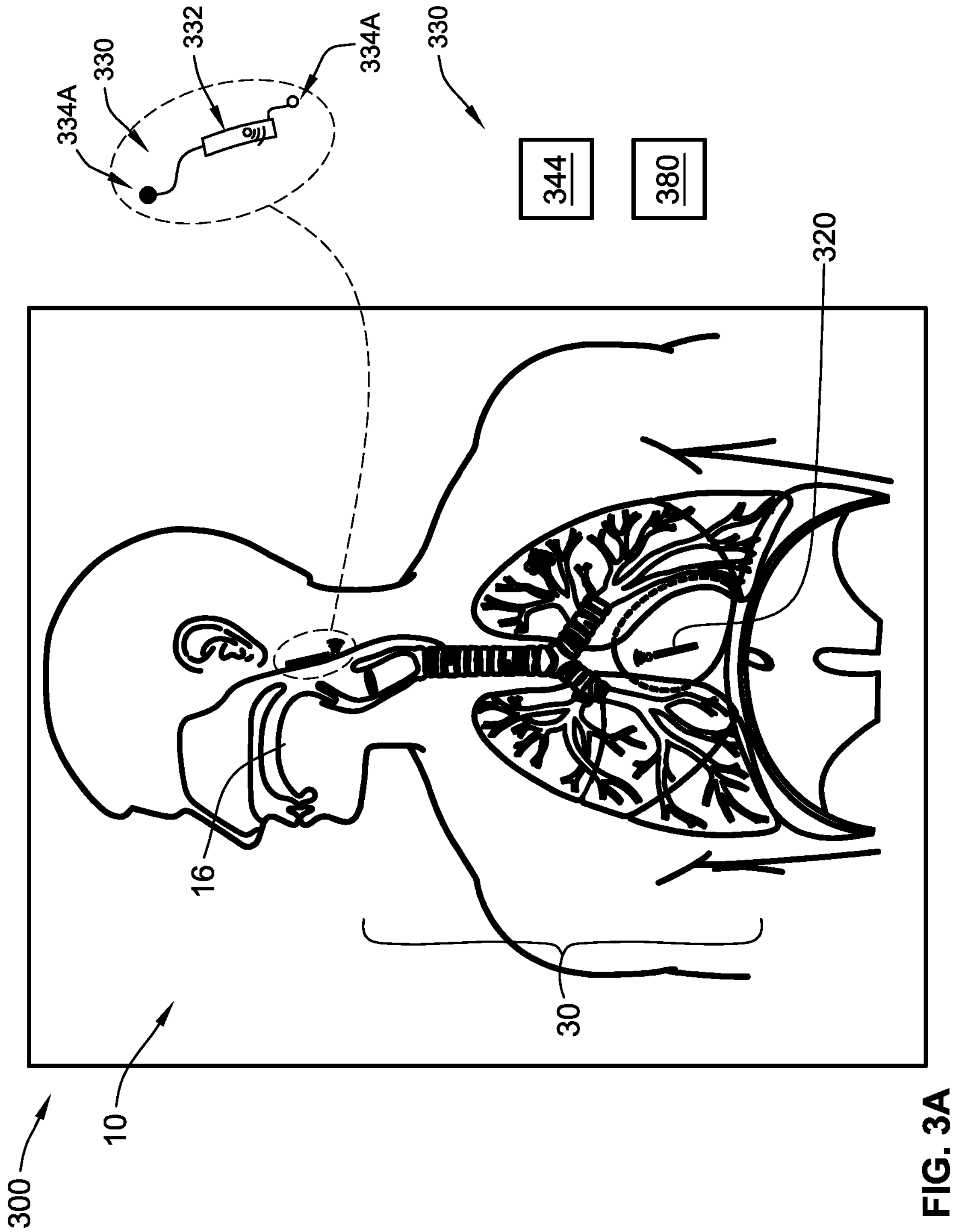
FIG. 3A is a schematic illustration of a respiration monitoring device positioned inside a user adjacent to a thoracic cavity and a stimulation device positioned inside the user adjacent to a tongue, according to some implementations of the present disclosure.

Referring to FIG. 3A, a system 300 that is the same as, or similar to, the system 100 (FIG. 2) includes a respiration monitoring device 320 and a stimulation device 330 that are implanted in the user 10. The respiration monitoring device 320 is the same as, or similar to, the respiration monitoring device 120 (FIG. 2) and is positioned in the thoracic cavity 30 of the user 10. It should be understood that the relative position of the respiration monitoring device 320 in the thoracic cavity 30 shown in FIG. 3A is merely exemplary, and that the respiration monitoring device 320 can be positioned at any suitable location in the thoracic cavity 30.

The stimulation device 330 is the same as, or similar to, the stimulation device 130 (FIG. 2) and includes a stimulator 332, a first lead 334A, and a second lead 334B. As shown, the stimulation device 330 is positioned generally adjacent to the tongue 16 of the user 10 such that the stimulator 332 can stimulate (e.g., provide an electrical current to) one or more branches of the hypoglossal nerve to cause movement of the muscle(s) in the tongue.

In the implementation of FIG. 3A, the respiration monitoring device 320 and the stimulation device 330 are powered by a magnetic field generator 344 that is the same as, or similar to, the magnetic field generator 144 (FIG. 2). The magnetic field generator 344 can be positioned in a mattress, a pillow, a bed, or any other suitable location for powering the respiration monitoring device 320 and/or the stimulation device 330. While one magnetic field generator 344 is shown in FIG. 3A, multiple magnetic field generators are contemplated. For example, a first magnetic field generator can be positioned generally adjacent to the stimulation device 330 (e.g., positioned in a pillow) and a second magnetic field generator can be positioned generally adjacent to the respiration monitoring device 320 (e.g., positioned in a mattress).

In some implementations, the respiration monitoring device 320 communicates directly with the stimulation device 330. The respiration monitoring device 320 and the stimulation device 330 can also communicate with an external device 380 that is the same as, or similar to, the external device 180 (FIG. 2) described herein. In some implementations, the respiration monitoring device 320 communicates directly with the external device 180, which in turn directly communicates with the stimulation device 330. In such implementations, the control system 110 (FIG. 2) described herein can be integrated in the external device 180. For example, data from the respiration monitoring device 320 is transmitted to the external device 180, which determines a stimulation time, and then the external device 180 communicates (e.g., sends a signal) to the stimulation device 330 to cause stimulation.

Figure 3B:
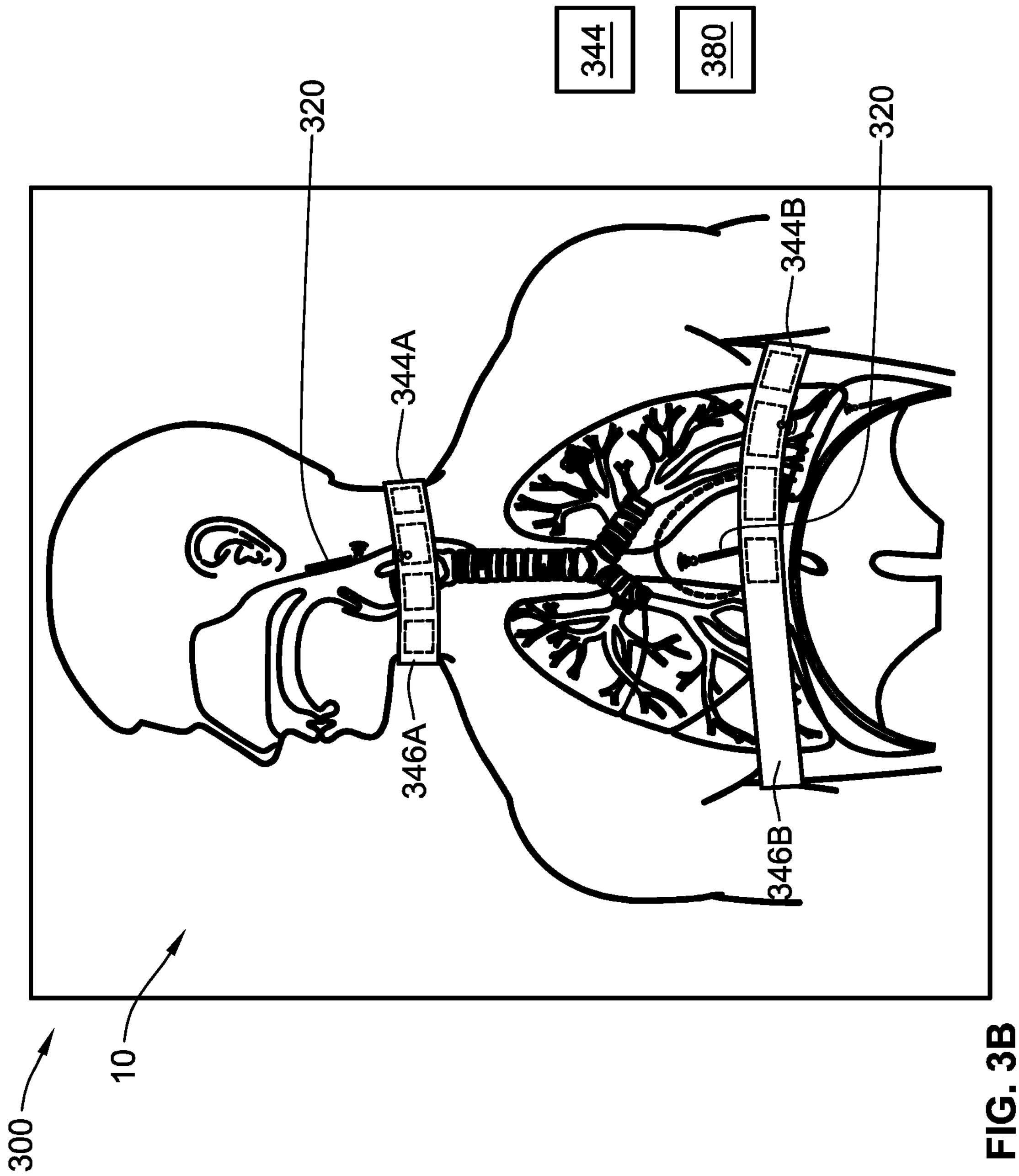
FIG. 3B is a schematic illustration of the respiration monitoring device and the stimulation device of FIG. 3A, a first wearable, and a second wearable, according to some implementations of the present disclosure.

Referring to FIG. 3B, in some implementations, the system 300 includes a first wearable 346A and a second wearable 346B that are the same as, or similar to, the wearable 146 (FIG. 2) of the system 100 described herein. As shown, the first wearable 346A is a collar that is generally positioned and secured around a neck of the user (e.g., using hook and loop fasteners). The first wearable 346A includes a first magnetic field generator 344A that is the same, or similar to, the magnetic field generator 144 (FIG. 2) described herein. Because the first wearable 346A is positioned general adjacent to the stimulation device 330, the first magnetic field generator 344A can wirelessly provide power to the stimulation device 330.

The second wearable 346B is a belt that is generally positioned and secured around a chest or waist of the user (e.g., using hook and loop fasteners). The second wearable 346B includes a second magnetic field generator 344B that is the same, or similar to, the magnetic field generator 144 (FIG. 2) described herein. Because the second wearable 346B is positioned general adjacent to the respiration monitoring device 320, the second magnetic field generator 344B can wirelessly provide power to the respiration monitoring device 320.

In some implementations, the control system 110 (FIG. 2) described herein can also be coupled to or integrated in the first wearable 346A and/or the second wearable 346B.

Figure 4:
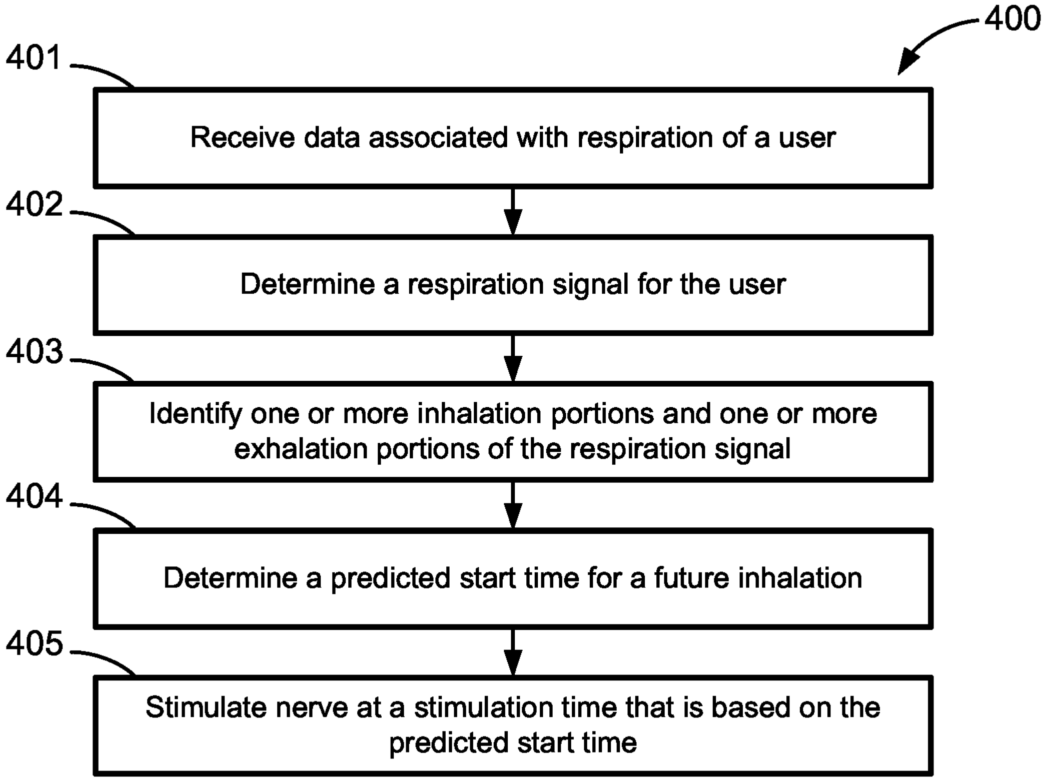
FIG. 4 is a process flow diagram for a method of aiding a user in breathing, according to some implementations of the present disclosure.

Referring to FIG. 4, a method 400 for aiding a user in breathing according to some implementations of the present disclosure is illustrated. For example, the method 400 can aid in preventing apneas from occurring. One or more steps of the method 400 can be implemented using any element or aspect of the system 100 (FIG. 2) described herein.

Step 401 of the method 400 includes receiving data associated with respiration of the user. For example, step 401 can include receiving data from the respiration monitoring device 120 (FIG. 2) that is positioned in the user (e.g., in the thoracic cavity of the user). In some implementations, the respiration data can be transmitted from the respiration monitoring device 120 and received by the memory device 114 for analysis by the control system 110. In other implementations, the respiration data can be transmitted from the respiration monitoring device 120 and received by the external device 180.

Figure 5:
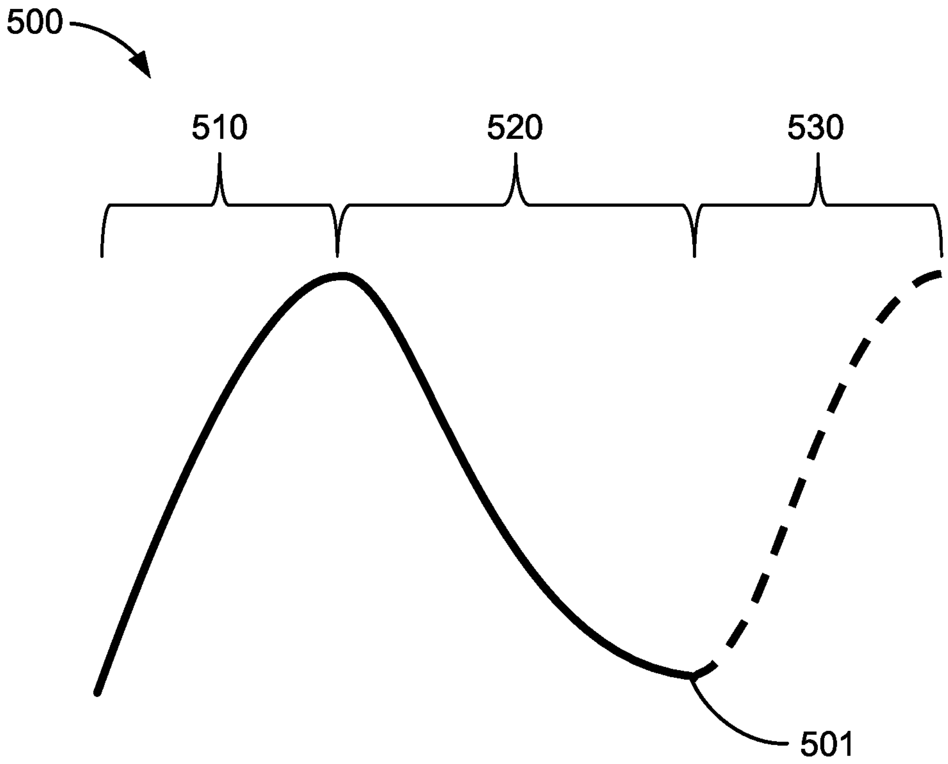
FIG. 5 is an exemplary respiration signal for a user, according to some implementations of the present disclosure.

Step 402 of the method 400 includes determining a respiration signal for the user based at least in part on the data associated with respiration of the user (step 401). The respiration signal is indicative of respiration (e.g., inhalation and exhalation) of the user and can be determined by, for example, the control system 110 (FIG. 2). Referring to FIG. 5, an exemplary respiration signal 500 for the user is illustrated.

Step 403 of the method 400 (FIG. 4) includes identifying one or more inhalation portions and one or more exhalation portions of the respiration signal. The inhalation portion(s) and exhalation portion(s) can be identified by the control system 110 (FIG. 2). Referring to FIG. 5, the respiration signal 500 includes an inhalation portion 510 and an exhalation portion 520. Generally, the inhalation portion 510 corresponds to the user breathing in (inspiration) and the exhalation portion 520 corresponds to the user is breathing out (expiration). In some implementations, the integral of the inhalation portion 510 of the respiration signal 500 is equal to the integral of the exhalation portion 520 of the respiration signal 500.

Step 404 of the method 400 includes determining a predicted start time for a future inhalation of the user. The predicted start time for the future inhalation can be determined by, for example, the control system 110 (FIG. 2). The predicted start time can be determined based at least in part on the data associated with respiration of the user (step 401) and/or historical respiration data. For example, the predicted start time can be determined using a machine learning algorithm that is trained using historical respiration data/signals to receive respiration data as an input and determine the predicted start time for the future inhalation as an output. Referring to FIG. 5, an exemplary future inhalation 530 is illustrated. As shown, the future inhalation 530 is the next actual inhalation that is subsequent to the first inhalation portion 510 identified during step 403 and immediately subsequent to the first exhalation portion 520. The future inhalation 530 has a predicted start time 501.

Step 405 of the method 400 (FIG. 4) includes providing electrical stimulation (e.g., using the stimulation devices described herein) to one or more branches of a nerve of the user at a stimulation time that is based at least in part on the predicted start time for the future inhalation of the user (step 404). For example, the stimulation time can be determined by the control system 110 (FIG. 2), which in turn wirelessly communicates with the stimulation device 130 to cause the stimulator 132 of the stimulation device 130 to stimulate one or more branches of a nerve of the user (e.g., one or more branches of the hypoglossal nerve of the user).

The stimulation time is prior to the predicted start time for the future inhalation of the user. For example, the stimulation time can be at least about 50 milliseconds, at least about 100 milliseconds, at least about 200 milliseconds, or at least about 300 milliseconds prior to the predicted start time for the future inhalation of the user. As another example, the stimulation time can be within 100 milliseconds, within 200 milliseconds, or within 300 milliseconds of the predicted start time for the future inhalation of the user. Because the stimulation time is just before the predicted start time for the next inhalation, the stimulation will cause the tongue to move and clear the airway just before the future inhalation, thereby aiding in preventing an apnea from occurring.

Figure 6:
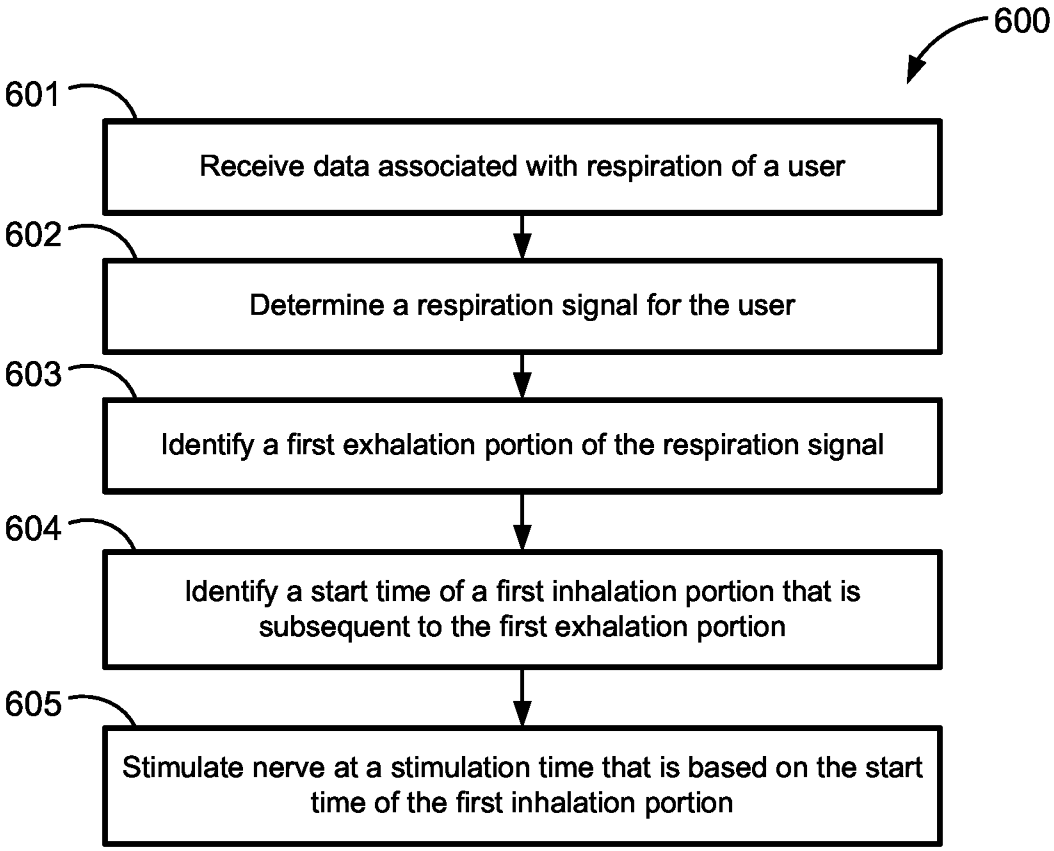
FIG. 6 is a process diagram for a method of aiding a user in breathing, according to some implementations of the present disclosure.

Referring to FIG. 6, a method 600 for aiding a user in breathing according to some implementations of the present disclosure is illustrated. For example, the method 600 can aid in preventing apneas from occurring. One or more steps of the method 600 can be implemented using any element or aspect of the system 100 (FIG. 2) described herein.

Step 601 of the method 600 is the same as, or similar to, step 401 of the method 400 (FIG. 4) described above and includes receiving data associated with respiration of the user. For example, step 601 can include receiving data from the respiration monitoring device 120 (FIG. 2) that is positioned in the user (e.g., in the thoracic cavity of the user). In some implementations, the respiration data can be transmitted from the respiration monitoring device 120 and received by the memory device 114 for analysis by the control system 110. In other implementations, the respiration data can be transmitted from the respiration monitoring device 120 and received by the external device 180.

Figure 7:
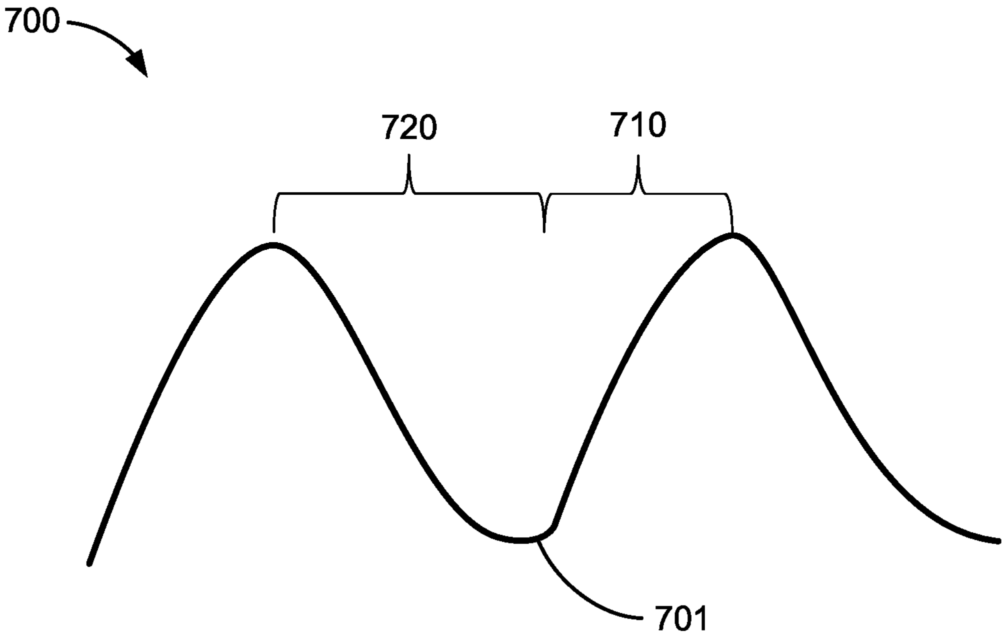
FIG. 7 is an exemplary respiration signal for a user, according to some implementations of the present disclosure.

Step 602 of the method 600 is the same as, or similar to, step 602 of the method 400 (FIG. 4) described above and includes determining a respiration signal for the user based at least in part on the data associated with respiration of the user (step 601). Referring to FIG. 7, an exemplary respiration signal 700 is illustrated.

Step 603 of the method 600 (FIG. 6) is similar to step 403 of the method 400 (FIG. 4) described above and includes identifying a first exhalation portion of the determined respiration signal for the user (step 602). The first exhalation portion in the determined respiration signal for the user can be determined using the control system 110 (FIG. 2). Referring to FIG. 7, an exemplary first exhalation portion 720 in the respiration signal 700 is shown.

Step 604 of the method 600 (FIG. 6) includes identifying a start time of a first inhalation portion of the respiration signal that is subsequent to the identified first exhalation portion (step 603). The start time can be identified by the control system 110 (FIG. 2) based at least in part on the determined respiration signal (step 602) and/or the received data associated with respiration of the user (step 601). Referring to FIG. 7, an exemplary first inhalation portion 710 of the respiration signal 700 is illustrated. As shown, the first inhalation portion 710 has a start time 701 that is immediately subsequent to the end of the first exhalation portion 720.

Step 605 of the method 600 includes stimulating a nerve of the user (e.g., using the stimulation devices described herein) at a stimulation time that is based on the identified start time of the first inhalation portion (step 604). For example, the stimulation time can be determined by the control system 110 (FIG. 2), which in turn wirelessly communicates with the stimulation device 130 to cause the stimulator 132 of the stimulation device 130 to stimulate one or more branches of a nerve of the user (e.g., one or more branches of the hypoglossal nerve of the user).

The stimulation time determined during step can be within 50 milliseconds, within 100 milliseconds, within 200 milliseconds, or within 300 milliseconds of the identified start time for the first inhalation portion (step 604).

Figure 8:
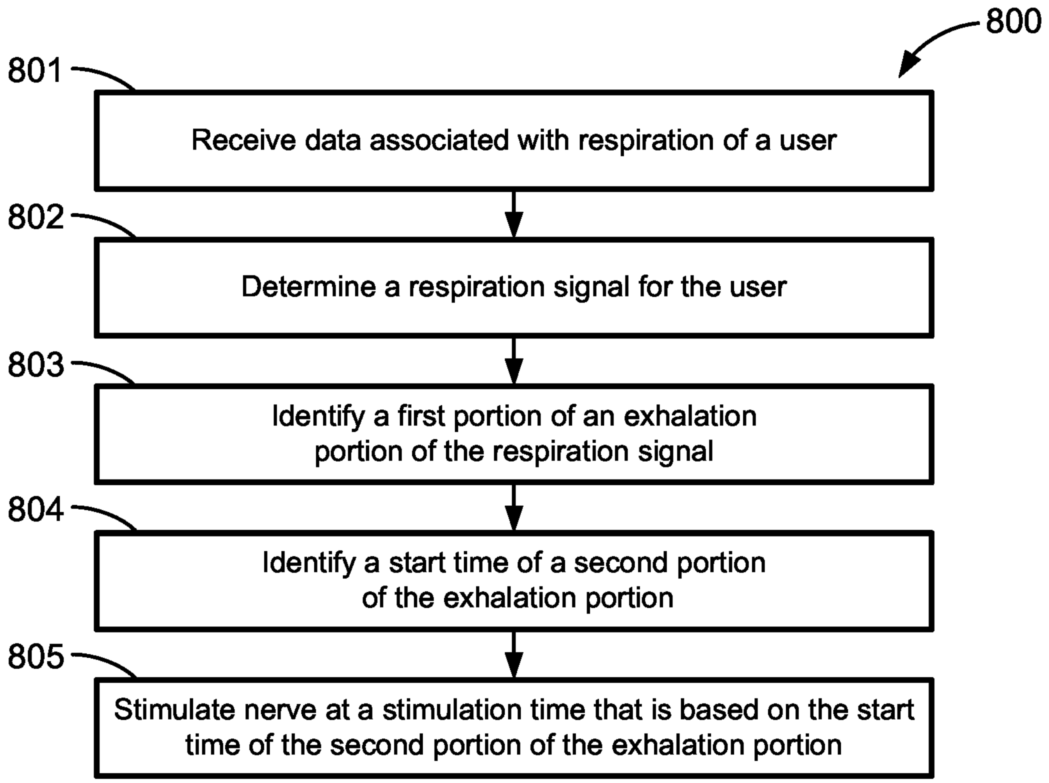
FIG. 8 is a process diagram for a method of aiding a user in breathing, according to some implementations of the present disclosure.

Referring to FIG. 8, a method 800 for aiding a user in breathing according to some implementations of the present disclosure is illustrated. For example, the method 800 can aid in preventing apneas from occurring. One or more steps of the method 800 can be implemented using any element or aspect of the system 100 (FIG. 2) described herein.

Step 801 of the method 800 is the same as, or similar to, step 401 of the method 400 (FIG. 4) described herein and includes receiving data associated with respiration of a user. For example, step 801 can include receiving data from the respiration monitoring device 120 (FIG. 2) that is positioned in the user (e.g., in the thoracic cavity of the user). In some implementations, the respiration data can be transmitted from the respiration monitoring device 120 and received by the memory device 114 for analysis by the control system 110. In other implementations, the respiration data can be transmitted from the respiration monitoring device 120 and received by the external device 180.

Figure 9:
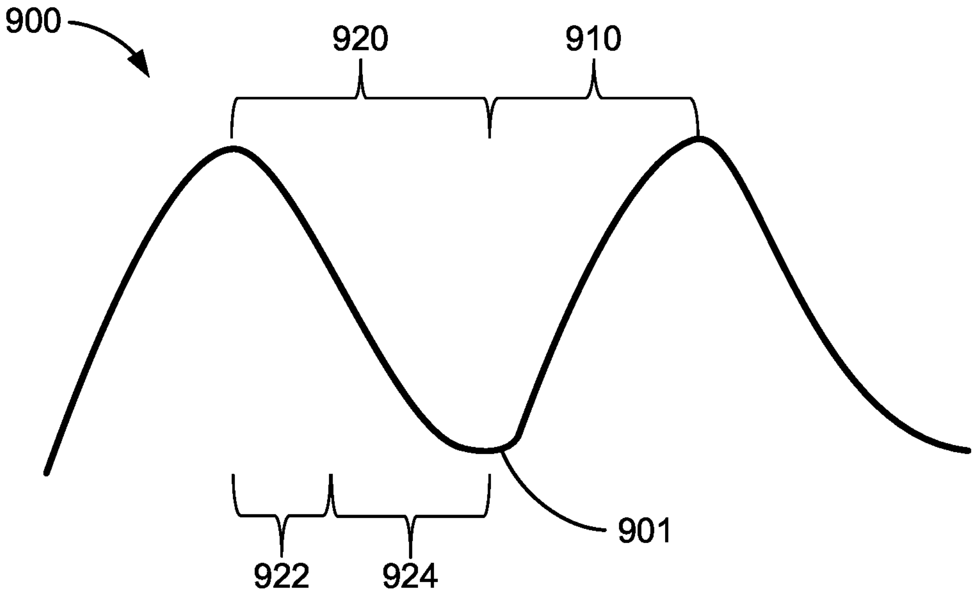
FIG. 9 is an exemplary respiration signal for a user, according to some implementations of the present disclosure.

Step 802 of the method 800 is the same as, or similar to, step 402 of the method 400 (FIG. 4) described herein and includes determining a respiration signal for the user. Referring to FIG. 9, an exemplary respiration signal 900 is illustrated.

Step 803 of the method 800 (FIG. 8) includes identifying a first portion of an exhalation portion of the determined respiration signal (step 802). The first portion of the exhalation portion can be identified by the control system 110 (FIG. 2). Referring to FIG. 5, the respiration signal 900 includes an exhalation portion 920. The exhalation portion 920 of the respiration signal 900 includes a first portion 922.

Step 804 of the method 800 (FIG. 8) includes identifying a start time of a second portion of the exhalation portion of the determined respiration signal (step 802). The second portion of the exhalation portion can be identified, for example, using the control system 110 (FIG. 2) described herein). In some implementations, the second portion of the exhalation portion is immediately subsequent to the identified first portion (step 803).

Referring to FIG. 9, the exhalation portion 920 of the respiration signal 900 includes a second portion 924. Together, the first portion 922 and the second portion 924 form the complete exhalation portion 920. The first portion 922 of the exhalation portion 920 can be, for example, at least about 10% of the exhalation portion 920, at least about 20% of the exhalation portion 920, at least about 30% of the exhalation portion 920, at least about 50% of the exhalation portion 920, at least about 60% of the exhalation portion 920, at least about 80% of the exhalation portion 920, etc. Conversely, the second portion 924 of the exhalation portion 920 can be, for example, at least about 90% of the exhalation portion 920, at least about 80% of the exhalation portion 920, at least about 70% of the exhalation portion 920, at least about 50% of the exhalation portion 920, at least about 40% of the exhalation portion 920, at least about 20% of the exhalation portion 920, etc.

Step 805 of the method 800 (FIG. 8) includes providing electrical stimulation (e.g., using the stimulation devices described herein) to one or more branches of a nerve of the user at a stimulation time that is based at least in part on a start time for the identified second portion of the exhalation portion of the respiration signal. For example, the stimulation time can be determined by the control system 110 (FIG. 2), which in turn wirelessly communicates with the stimulation device 130 to cause the stimulator 132 of the stimulation device 130 to stimulate one or more branches of a nerve of the user (e.g., one or more branches of the hypoglossal nerve of the user).

The stimulation time is subsequent to the start time of the identified second portion of the exhalation portion (step 804), but prior to a next inhalation portion of the respiration signal (e.g., the next actual inhalation of the user). The stimulation time can be, for example, within 50 milliseconds, within 100 milliseconds, within 200 milliseconds, or within 300 milliseconds of the start time for the second portion of the exhalation portion. Because the stimulation time is before the \start time for the next inhalation, the stimulation will cause the tongue to move and clear the airway just before the future inhalation, thereby aiding in preventing an apnea from occurring.

In some implementations, the methods 400, 600, and 800 described herein can also include analyzing the data associated with respiration of the user to determine a number of events the user experienced from a period of time (e.g., using the control system 110 (FIG. 2)). The events can include, for example, apneas, hypopneas, hyperpneas, or any combination thereof. The period of time can be, for example 15 minutes, 30 minutes, 45 minutes, an hour, two hours, three hours, five hours, seven hours, etc.

In such implementations, the methods 400, 600, and 800 described herein can also include comparing the determined number of events with a threshold and in response to the determined number of events exceeding the threshold, causing the stimulation device to change one or more parameters of the electrical stimulation being provided to the one or more branches of the nerve. The threshold can be a number of events per hour (e.g., 3 events per hour, 5 events per hour, 10 events per hour, 20 events per hour, etc.). The one or more parameters of the electrical stimulation can include, for example, an amount of time during a breath that the electrical stimulation is provided, a percentage of an amount of time during a breath when the electrical stimulation is provided, a percentage of an amount of time during inhalation when the electrical stimulation is provided, a percentage of an amount of time during exhalation when the electrical stimulation is provided, frequency, intensity, duration, dwell time, rise time in a pulse, a ratio of on-time to an off-time, or any combination thereof.

One or more elements or aspects or steps, or any portion(s) thereof, from one or more of any of the claims below can be combined with one or more elements or aspects or steps, or any portion(s) thereof, from one or more of any of the other claims below, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A system for aiding a user in breathing during a sleep session of the user, the system comprising:

a respiration monitoring device configured to be positioned inside the user adjacent to a thoracic cavity of the user, the respiration monitoring device including a sensor configured to generate respiration data associated with respiration of the user;

a stimulation device configured to be positioned inside the user adjacent to a tongue of the user, the stimulation device including a stimulator that is configured to provide electrical stimulation to one or more branches of a nerve of the user that are adjacent to the tongue of the user, the stimulation device being physically separated from the respiration monitoring device and communicatively coupled with the respiration monitoring device via a wireless communication protocol;

an external sensor configured to be positioned outside the user, the external sensor configured to generate physiological data;

a memory storing machine-readable instructions; and a control system including one or more processors configured to execute the machine-readable instructions to:

determine, using the generated physiological data, if the respiration monitoring device has failed;

responsive to determining that the respiration monitoring device has failed, cause the stimulation device to automatically provide electrical stimulation to the one or more branches of the nerve at a predetermined duty cycle;

responsive to determining that the respiration monitoring device has not failed:

determine, based at least in part on the generated respiration data associated with the respiration of the user, a respiration signal for the user;

identify, within the respiration signal, one or more inhalation portions and one or more exhalation portions;

analyze the generated respiration data to determine a number of respiration events the user experienced over a period of time during the sleep session;

based at least in part on the number of respiration events, determine one or more parameters for an electrical stimulation to be provided to the one or more branches of the nerve;

based at least in part on the identified one or more inhalation portions, determine a predicted start time for a future inhalation of the user; and cause the stimulation device to provide electrical stimulation based at least in part on the one or more parameters to the one or more branches of the nerve at a stimulation time that is based at least in part on the predicted start time for the future inhalation of the user.

2. The system of claim 1, wherein the stimulation time is the predicted start time for the future inhalation of the user.

3. The system of claim 1, wherein the stimulation time is at least about 50 milliseconds prior to the predicted start time for the future inhalation of the user.

4. The system of claim 1, wherein the stimulation time is within 100 milliseconds of the predicted start time for the future inhalation of the user.

5. The system of claim 1, wherein the future inhalation of the user is a next inhalation of the user.

6. The system of claim 1, wherein each of the one or more inhalation portions corresponds to the user breathing in and each of the one or more exhalation portions correspond to the user breathing out.

7. The system of claim 1, wherein the nerve is a hypoglossal nerve.

8. The system of claim 1, wherein the control system is further configured to execute the machine-readable instructions to:

compare the determined number of respiration events with a threshold, wherein the determining the one or more parameters is based at least in part on the determined number of respiration events exceeding the threshold.

9. The system of claim 8, wherein the period of time is an hour.

10. The system of claim 8, wherein the threshold is ten respiration events per hour.

11. The system of claim 8, wherein the one or more parameters of the electrical stimulation include an amount of time during a breath that the electrical stimulation is provided, a percentage of an amount of time during a breath when the electrical stimulation is provided, a percentage of an amount of time during inhalation when the electrical stimulation is provided, a percentage of an amount of time during exhalation when the electrical stimulation is provided, frequency, intensity, duration, dwell time, rise time in a pulse, a ratio of on-time to an off-time, or any combination thereof.

12. The system of claim 1, wherein the control system is coupled to a belt configured to be worn by the user.

13. The system of claim 12, further comprising a power supply coupled to the belt, the power supply being configured to wirelessly power the respiration monitoring device.

14. The system of claim 1, wherein respiration monitoring device includes a built-in power supply.

15. The system of claim 1, wherein the wireless communication protocol is Bluetooth.

16. The system of claim 1, further comprising a second respiration monitoring device, wherein data from the second respiration monitoring device is combined with the generated respiration data to determine the respiration signal for the user.

17. The system of claim 16, wherein both the second respiration monitoring device and the respiration monitoring device are provided in separate housings and configured to be positioned inside the user adjacent to the thoracic cavity of the user.

18. A method for aiding a user in breathing during a sleep session, the method comprising:

receiving respiration data associated with respiration of a user from a respiration monitoring device, the respiration monitoring device being positioned inside the user adjacent to a thoracic cavity of the user;

receiving physiological data from an external sensor, the external sensor being positioned outside the user;

determining, using the physiological data, if the respiration monitoring device has failed;

responsive to determining that the respiration monitoring device has failed, causing a stimulation device to automatically provide electrical stimulation to one or more branches of a nerve of the user at a predetermined duty cycle;

responsive to determining that the respiration monitoring device has not failed:

determining, based at least in part on the respiration data associated with respiration of the user, a respiration signal for the user;

determining, based at least in part on the respiration signal, a predicted start time for a future inhalation of the user;

analyzing the respiration data to determine a number of respiration events the user experienced over a period of time during the sleep session;

based at least in part on the determined number of respiration events, determining one or more parameters for an electrical stimulation to be provided to the one or more branches of the nerve of the user; and causing the stimulation device to provide the electrical stimulation based at least in part on the one or more parameters to the one or more branches of the nerve of the user at the predicted start time, the stimulation device being positioned inside the user adjacent to a tongue of the user and being physically separated from the respiration monitoring device and communicatively coupled with the respiration monitoring device via a wireless communications protocol.

19. The method of claim 18, wherein the respiration signal includes one or more inhalation portions and one or more exhalation portions.

20. The method of claim 19, wherein the determining the predicted start time for the future inhalation of the user is based at least in part on the one or more inhalation portions of the respiration signal.

* * * * *